United States Patent [19]

Lin

[11] Patent Number: 5,439,463

[45] Date of Patent: Aug. 8, 1995

[54] SPINAL CLAMPING DEVICE

[76] Inventor: Chih-I Lin, 513 S. Golden Pardos Dr., Diamond Bar, Calif. 10765

[21] Appl. No.: 151,017

[22] Filed: Nov. 12, 1993

[51] Int. Cl.⁶ .............................................. A61B 17/70
[52] U.S. Cl. ................................................... 606/61
[58] Field of Search ...................... 606/61, 60, 69, 71, 606/105

[56] References Cited

U.S. PATENT DOCUMENTS

| 5,002,542 | 3/1991 | Frigg | 606/61 |
| 5,092,893 | 3/1992 | Smith | 606/61 |
| 5,176,678 | 1/1993 | Tsou | 606/61 |

Primary Examiner—Tamara L. Graysay
Attorney, Agent, or Firm—Bacon & Thomas

[57] ABSTRACT

A spinal clamping device includes a spinal clamping member, a clamping adjusting member, a distance adjusting bar, and a distance adjusting and fastening member. The spinal clamping member has a clamping portion and a connecting portion. The clamping adjusting member has a clamping portion and a connecting portion provided with a rough surface formed on a predetermined portion of a surface thereof. The distance adjusting bar has one end fastened with the connecting portion of the spinal clamping member and another end that is provided with a rough surface formed on a predetermined portion of a surface thereof. The rough surfaces of the clamping adjusting member and the distance adjusting bar are adjustably stacked and fastened by the distance adjusting and fastening member.

6 Claims, 3 Drawing Sheets

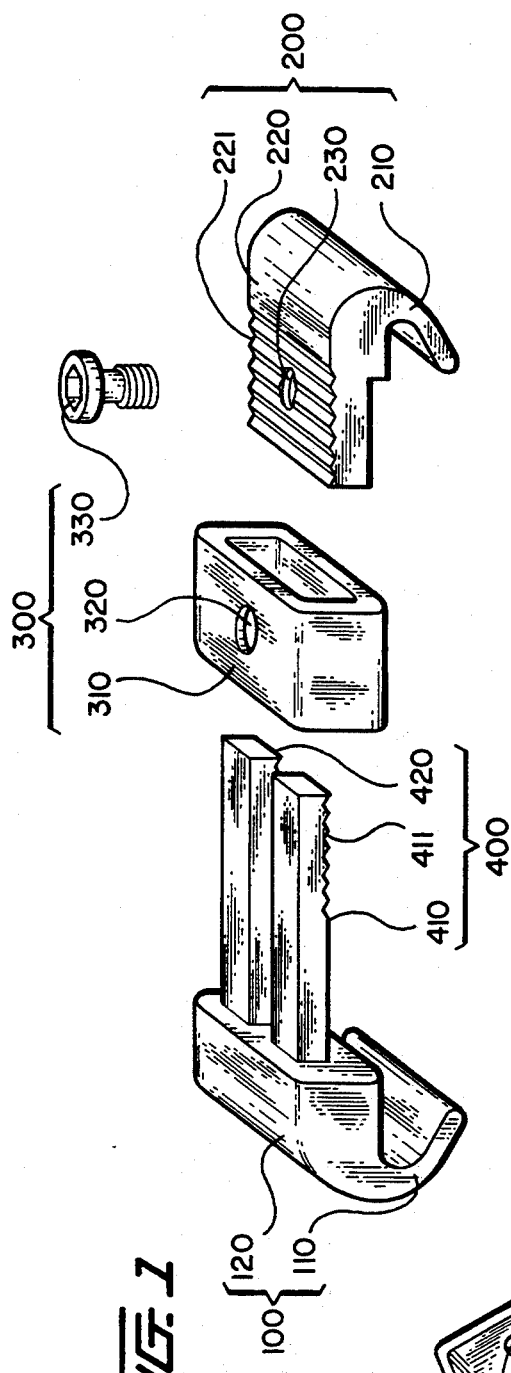
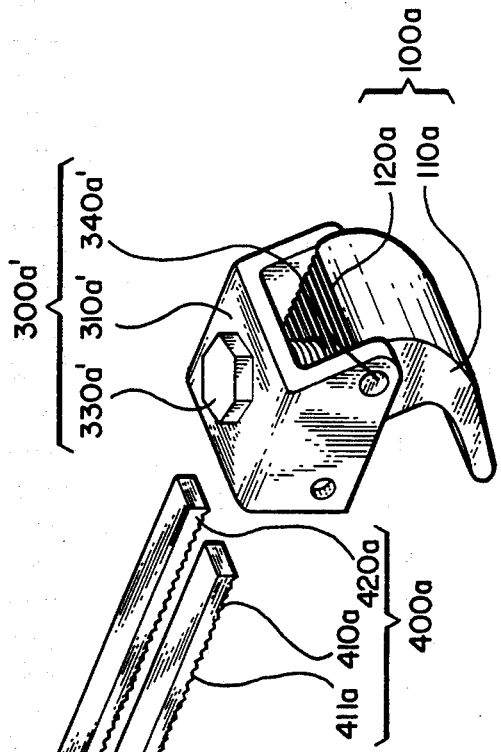
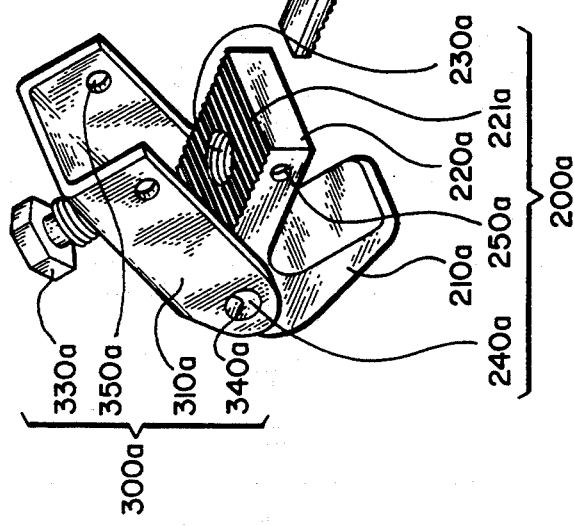

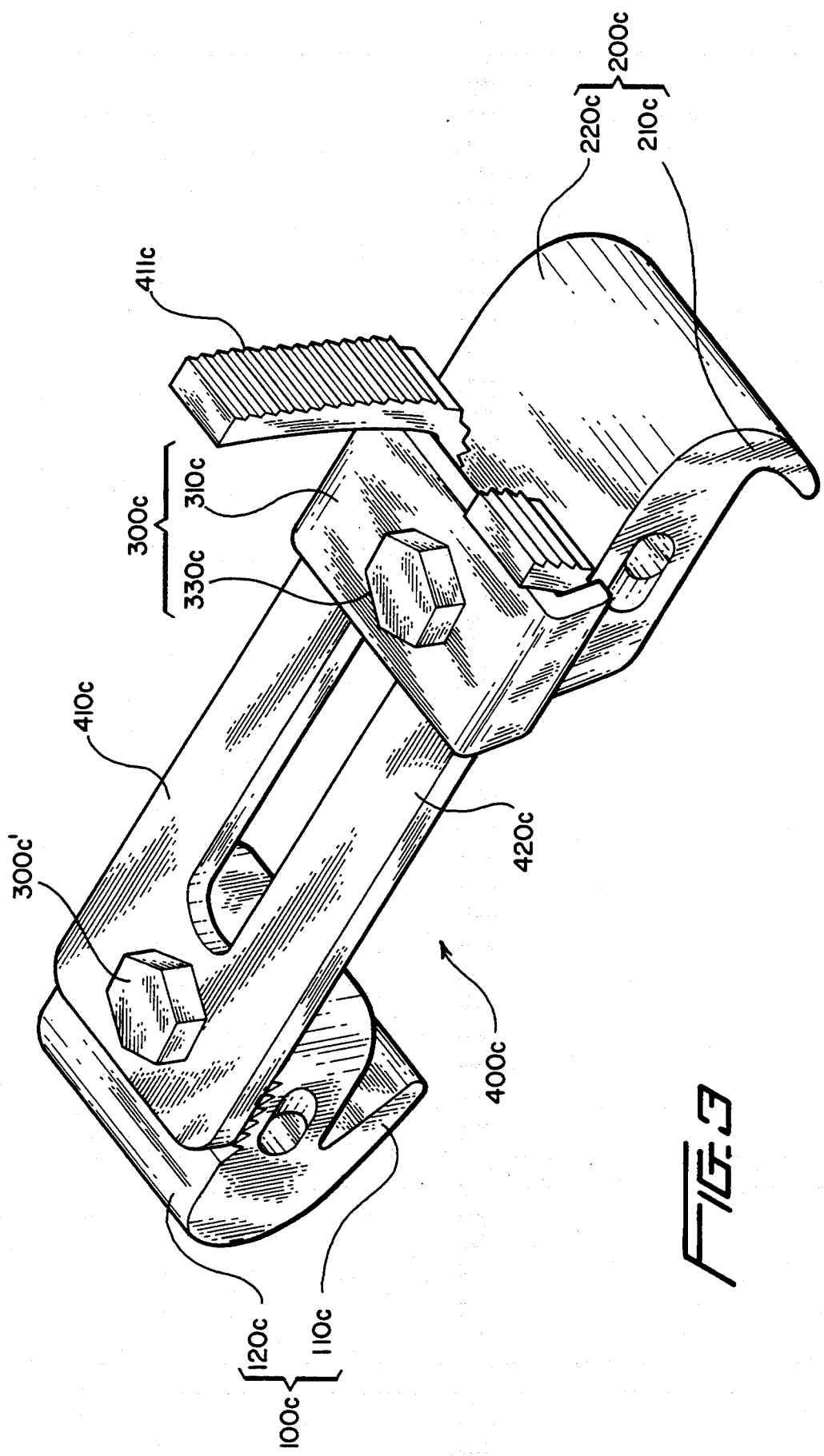

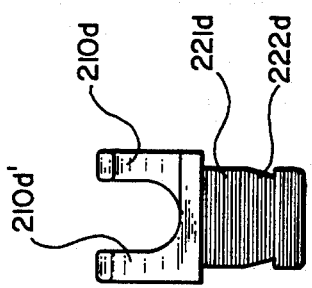
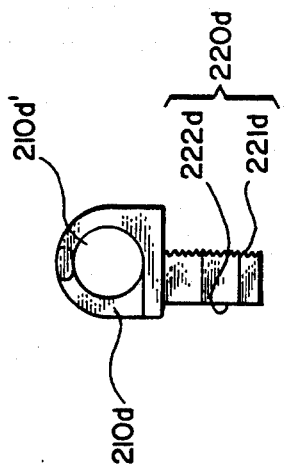
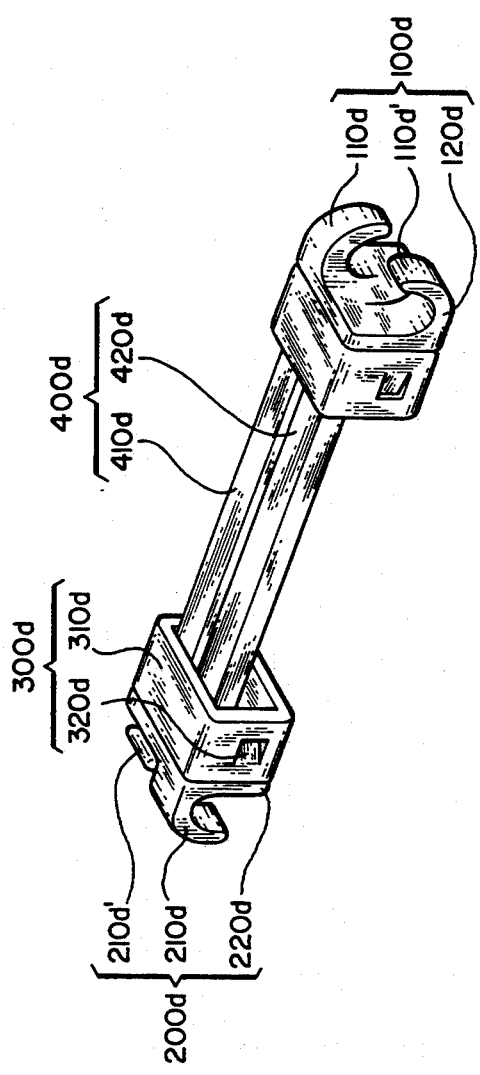
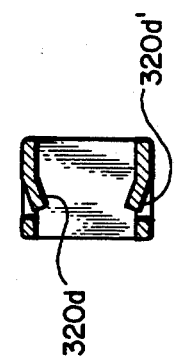

SPINAL CLAMPING DEVICE

FIELD OF THE INVENTION

The present invention relates generally to an orthopedic device, and more particularly to a spinal clamping device.

BACKGROUND OF THE INVENTION

The spinal clamping systems of the prior art are generally composed of two hooked devices for fixing a disabled vertebra and of fasteners such as nuts and bolts for fastening the two hooked devices holding the disabled vertebra. The case in point is the interlaminar clamp system bearing the trademark of HALIFAX and made by the AME Corporation of the United States. Such spinal clamping systems of the prior art are defective in design in that the fastening effect of the hooked devices is often seriously undermined by the fact that the spinal movement can cause the nuts and the bolts to become loosened. Such defective design of the prior art spinal clamping systems is discussed by Ronald Moskovich, et al. in an article entitled "Altantoaxial Arthrodesis using Interlaminar Clamps", which was published in SPINE, 17 (3), 261 (1992). For details, please refer to FIG. 5 and the accompanying text therefore in the article.

In addition, the spinal clamping systems of the prior art are further limited in that they can not be used to bring about an auxiliary fixation between two vertebral locking rods.

With a view to overcoming the shortcomings of the spinal clamping systems of the prior art, this inventor of the present invention developed several improved spinal clamping systems, which were disclosed respectively in the U.S. patent application Ser. Nos. 08/004,612 (filing date: Jan. 14, 1993), 08/004,609 (filing date: Jan. 14, 1993) and 08/004,610 (filing date: Jan. 14, 1993). The improved spinal clamping system, which was disclosed in the U.S. patent application Ser. Nos. '612 and '610, is of a dual-layer system and composed of screws and slotted plates for use in adjusting the distance between the two hooked portions. The improved spinal clamping system disclosed in the U.S. patent application Ser. No. '609 is of a reversible clamping system and composed of reversible clamping members having a plurality of bevel clamping slots for use in adjusting the distance between two hooked portions. These improved spinal clamping systems described above are limited in design in that the distance between the two hooked portions can not be adjusted at will, and that the dual-layer locking effect of the vertebra is often compromised by the excessively protruded portions of the systems.

SUMMARY OF THE INVENTION

It is therefore the primary objective of the present invention to provide a spinal clamping device which is made up of multibranched, horizontal and parallel components.

It is another objective of the present invention to provide a spinal clamping device which is composed of clamping member, clamping adjusting member, distance adjusting and fastening member and distance adjusting bar.

The foregoing objectives of the present invention are attained by a spinal clamping device, which comprises a spinal clamping member made up of a clamping portion and a connecting block, a clamping adjusting member made up of a clamping portion and a connecting block having a surface which is at least partially rough, a multibranched adjusting bar having one end that is fastened with the connecting block of the spinal clamping member and having another end with a surface which is at least partially rough and which is stacked with the rough surface of the connecting block of the clamping adjusting member, and a distance adjusting and fastening member for fastening the adjusting bar with the connecting block of the clamping adjusting member.

The foregoing objectives, structures and functions of the present invention will be more readily understood by studying the following detailed description of the present invention in conjunction with the drawings provided herewith.

BRIEF DESCRIPTION OF THE DRAWINGS

FIG. 1 shows an exploded view of a preferred embodiment of the present invention.

FIG. 2 shows an exploded view of another preferred embodiment of the present invention.

FIG. 3 shows a perspective view of the present invention in combination.

FIG. 4a shows another perspective view of the present invention in combination.

FIG. 4b shows a side elevational view of the distance adjusting bar of the present invention.

FIG. 4c shows a left elevational view of the distance adjusting and fastening member of the present invention.

FIG. 4d shows a side elevational view of the clamping adjusting member of the present invention.

FIG. 4e shows a top view of the clamping adjusting member of the present invention.

DETAILED DESCRIPTION OF THE INVENTION

As shown in FIG. 1, a preferred embodiment of the present invention comprises a clamping member 100, a clamping adjusting member 200, a distance adjusting and fastening member 300, and a distance adjusting bar 400.

The clamping member 100 is composed of a hook-shaped clamping portion 110 and a connecting portion 120. The clamping adjusting member 200 has a hook-shaped clamping portion 210, a connecting portion 220 having a corrugated surface 221, and a fixing threaded hole 230. The distance adjusting and fastening member 300 is provided with a clamping sleeve 310, a clamping hole 320, and a clamping screw 330. The distance adjusting bar 400 comprises two distance adjusting arms 410 and 420, with the distance adjusting arms 410 and 420 each having a corrugated surface 411.

The connecting block 120 of the clamping member 100 is made integrally with the two distance adjusting arms 410 and 420. The clamping member 100, the clamping adjusting member 200 and the distance adjusting and fastening member 300 are joined together such that the corrugated surfaces 411 of the distance adjusting arms 410 and 420 engage the corrugated surface 221 of the connecting block 220 of the clamping adjusting member 200 so that the clamping member 100 and the clamping adjusting member 200 are spaced appropriately. The clamping member 100 and the clamping adjusting member 200 are held securely together by means of the distance adjusting and fastening member 300, which is fitted over the connecting block 220 of the clamping adjusting member 200 and the distance adjusting arms 410 and 420 such that the clamping hole 320 of the distance adjusting and fastening member 300 is aligned with the fixing threaded hole 230 of the connecting block 220 of the clamping adjusting member 200. The clamping screw 330 is screwed into the fixing threaded hole 230 and the clamping hole 320.

As shown in FIG. 2, another preferred embodiment of the present invention comprises a clamping member 100a, a clamping adjusting member 200a, two distance adjusting and fastening members 300a and 300a', and a distance adjusting bar 400a. All other reference numerals shown in FIG. 2 are similar in definition to those shown in FIG. 1. The second preferred embodiment, as shown in FIG. 2, is different from the first preferred embodiment, as shown in FIG. 1, in that the distance adjusting and fastening member 300a is provided with an axial hole 340a which is fitted rotatably over a short shaft 240a of the clamping adjusting member 200a, and that the former is provided with a round tenon 350a, extending from each side portions 310a, that is engageable with a round mortise 250a. As the distance adjusting arms 410a and 420a are caused to engage appropriately the corrugated surface 221a of the clamping adjusting member 200a, the distance adjusting and fastening member 300a is pivoted about the short shaft 240a until such time when the round tenon 350a is received in the round mortise 250a. Thereafter, the screw 330a is fastened onto the fixing threaded hole 230a. Of course, a similar arrangement is provided for distance adjusting and clamping member 300a' with corresponding reference numerals being designated with a prime.

A third preferred embodiment of the present invention is shown in FIG. 3, in which all reference numerals are similar in definition to those of FIG. 1. The third preferred embodiment of the present invention basically differs from the first preferred embodiment of the present invention in that the former is provided with two distance adjusting arms 410c and 420c which are joined together as a unitary body, and that the former is provided with an additional fastening screw 300c' to fasten one end of a distance adjusting bar 400c to a clamping member 100c.

In FIGS. 4a–4e, a clamping member 100d' is shown to comprise another clamping portion 100d'' while the clamping adjusting member 200d is shown to comprise another clamping portion 210d''. A recessed portion of a clamping adjusting member 200d is designated as 222d. The distance adjusting and fastening member 300d has an elastic retaining piece 320d or 320d' engageable with the recessed portion 222d. All other reference numerals are similar in definition to those of FIG. 1. The assembly of the preferred embodiment shown in FIGS. 4a–4e is explained hereinafter.

The corrugated surface 221d of the clamping adjusting member 200d is caused to engage appropriately the corrugated surface 411d of the distance adjusting bar 400d before the distance adjusting and fastening member 300d is fitted thereover in such a manner that the elastic retaining piece 320d or 320d' is retained in the recessed portion 222d of the clamping adjusting member 200d.

The fourth preferred embodiment, as shown in FIGS. 4a–4e, differs from the previous preferred embodiments of the present invention in that the former is provided with the clamping member and the clamping adjusting member, which are provided respectively with a double-hooked clamping portion, and that the former is provided with the distance adjusting and fastening member which has an elastic retaining piece that is retained in the clamping portion of the clamping member or the recessed portion of the clamping member adjusting block. It must be noted here that additional fastening means may be used to reinforce the fastening of the clamping member and the distance adjusting and fastening member or the clamping adjusting member and the distance adjusting and fastening member.

The clamping portion of the clamping member of the present invention is preferably integral with the clamping member and may be either single-hooked or multihooked. The connecting portion of the clamping adjusting member of the present invention is preferably integral with the clamping adjusting member. If necessary, the connecting portion may be reinforced by an additional fastening device, such as a threaded hole engageable with a fastener.

The connecting block of the clamping adjusting member has a surface which is at least partially corrugated. Similarly, the distance adjusting arms of the distance adjusting bar have a surface which is at least partially corrugated. Such corrugated surfaces serve to provide a better fastening contact between the connecting portion of the clamping adjusting member and the distance adjusting arms. The grooves and the ridges of the corrugated surfaces are preferably parallel to one another. The grooves and the ridges of the corrugated surface of the connecting portions of the clamping adjusting member are preferably perpendicular to the distance adjusting arms.

The distance adjusting bar of the present invention is a unitary body made up of two or more distance adjusting arms parallel to one another. The grooves and the ridges of the corrugated surface of the distance adjusting bar are preferably perpendicular to the longitudinal axis of the distance adjusting bar.

The distance adjusting and fastening member of the present invention may be a known fastening device, such as a retaining device, a threaded fastener, a mortise-tenon device, etc.

The connecting portion of the clamping member of the present invention is preferably integral with the clamping member. However, the connecting portion and the clamping member may be made separately and then united together by means of a threaded fastener, a retaining device, a mortise-tenon device, etc. In addition, the connecting portion and the clamping member may be joined together in such a way similar to the one that is used to fasten the distance adjusting bar and the connecting portion of the clamping adjusting member.

The spinal clamping device of the present invention may be used as a device for fixing and retrieving two different vertebrae, or an auxiliary and horizontal fixation device for clamping a vertebra and a vertebral fixation rod or two vertebral fixation rods. In addition, the spinal clamping device of the present invention may be used in conjunction with other known vertebral fixation devices for fixing and retrieving a deformed vertebra.

Prior to a surgical application, the clamping member, the clamping adjusting member, the distance adjusting and fastening member, and the distance adjusting bar of the present invention must be first united together, with the distance adjusting and fastening member remaining unfastened so as to permit the distance between the clamping member and the clamping adjusting member to be adjusted if necessary. The assembled spinal clamping device of the present invention is then surgically implanted such that the clamping portions of the clamping member and the clamping adjusting member are used respectively to hold firmly a vertebra and/or a vertebral fixation rod. Thereafter, the distance between the clamping member and the clamping adjusting member is adjusted appropriately by a hand tool before the distance adjusting and fastening member is tightened so as to ensure that the clamping member, the clamping adjusting member, the distance adjusting and fastening member, and the distance adjusting bar are all held together securely.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. A spinal clamping device comprising:
    a spinal clamping member including a hook-shaped clamping portion adapted to extend about a first vertebral fixation rod and a connecting portion;
    a clamping adjusting member including a hook-shaped clamping portion adapted to extend about a second vertebral fixation rod that is arranged substantially parallel to the first vertebral fixation rod and a connecting portion which has a rough surface formed on a predetermined portion of a surface thereof;
    a multibranched distance adjusting bar having one end that is fastened with said connecting portion of said spinal clamping member and having another end that is provided with a rough surface formed on a predetermined portion of a surface thereof, with said rough surface being engageable frictionally with said rough surface of said connecting portion of said clamping adjusting member; and
    a distance adjusting and fastening means for fixing said rough surface of said connecting portion of said clamping adjusting member and said rough surface of said multibranched distance adjusting bar whereby said spinal clamping device can clamp the first and second vertebral fixation rods together.

2. The spinal clamping device of claim 1 wherein said rough surface of said connecting portion of said clamping adjusting member and said rough surface of said distance adjusting bar are composed of a plurality of grooves and ridges, which are parallel to one another and substantially perpendicular to a longitudinal axis of said multibranched distance adjusting bar.

3. The spinal clamping device of claim 1 wherein said distance adjusting and fastening means comprises a threaded fastener.

4. The spinal clamping device of claim 1 wherein said distance adjusting and fastening means comprises a sleeve slidably mounted about said multibranched distance adjusting bar and a fastening member for securing said sleeve to said clamping adjusting member.

5. The spinal clamping device of claim 1 wherein the the distance adjusting and fastening means and said clamping adjusting member are pivotally interconnected.

6. The spinal clamping device of claim 1 wherein the clamping portion of each of said spiral clamping member and said clamping adjusting member is comprised of multiple hook-shaped members.

* * * * *